United States Patent [19]

Hagen et al.

[11] Patent Number: 4,960,592

[45] Date of Patent: Oct. 2, 1990

[54] LANOLIN AND LANOLIN OIL SKIN TREATMENT COMPOSITION

[75] Inventors: Resheda Hagen, Oak Ridge, Tenn.; Gabriel Barnett, New York, N.Y.

[73] Assignee: Lanocare Laboratories, Oak Ridge, Tenn.

[21] Appl. No.: 338,673

[22] Filed: Apr. 17, 1989

[51] Int. Cl.$^5$ .................. A61K 35/36; A61K 7/48
[52] U.S. Cl. ........................... 424/537; 514/844; 514/846; 514/847; 514/873; 514/887; 514/169
[58] Field of Search ............... 424/95, 844, 846, 847, 424/873, 887

[56] References Cited

U.S. PATENT DOCUMENTS 3,666,857  5/1972  Russell .................. 514/873
4,722,843  2/1988  Vinson .................. 514/847

FOREIGN PATENT DOCUMENTS 0006425  1/1978  Japan .................. 424/95
2169509  7/1986  United Kingdom ........ 514/847

OTHER PUBLICATIONS

*Cosmetics & Science Technology*, Wiley-Interscience, New York, 1972, pp. 182-183.

*Primary Examiner*—Jacqueline Stone
*Assistant Examiner*—Jean C. Witz
*Attorney, Agent, or Firm*—Sherman and Shalloway

[57] ABSTRACT

A composition for the treatment of dry skin comprises a mixture of lanolin and lanolin oil. Preferably, the composition contains about 75% by weight of lanolin and about 25% by weight of lanolin oil.

12 Claims, No Drawings

LANOLIN AND LANOLIN OIL SKIN TREATMENT COMPOSITION

BACKGROUND OF THE INVENTION

1. Field Of The Invention:

The present invention relates to skin treatment compositions and especially to emollient compositions. More particularly, the present invention relates to compositions comprising lanolin and lanolin oil.

2. Description Of The Prior Art:

Under normal conditions, the water content and vapor pressure of the epidermis are higher than the surrounding air and water evaporates from the surface of the skin. Skin becomes dry due to excessive loss of water from the stratum corneum when exposed to low relative humidities, insufficient hydration from the lower epidermal layers and/or air movement.

Frazier et al., A Formulary For External Therapy of the Skin, Charles C. Thomas, Springfield, Illinois (1954), pp. 55-69, defined an emollient material as one which prevents or relieves dryness of the skin. Strianse, S.J., "Hand Creams and Lotions" in Sagarin, E., Cosmetics: Science and Technology, Wiley-Interscience, New York (1972), p. 180, defined an emollient as an "agent which, when applied to a dry or inflexible corneum, will effect a softening of that tissue by inducing rehydration".

Skin dryness, and reduced flexibility, of the stratum corneum cannot be corrected by the addition of oily materials, but the skin will become flexible when rehydrated, even in the absence of oily materials.

It is the decrease in the water content of the stratum corneum which is the main cause of the dry feeling in chapped skin. Inasmuch as the water which diffuses from the dermis to the upper layers is limited in quantity and insufficient to balance the water lost from the skin surface by evaporation, especially in low relative humidities, the skin approaches a certain degree of inflexibility and stiffness. It is here that an emollient finds its maximum use, in serving as an occlusive agent, i.e., a hydrophobic material which reduces or prevents passage of water into or through a film of these substances. The occlusive material acts as a barrier to evaporation of water from the skin surface, and hence permits rehydration of the corneum. In addition, the emollient imparts slip but does not necessarily soften the skin because of its "lubricating" properties. Barnett, G., "Emollient Creams and Lotions" in Sagarin, E., Cosmetics: Science and Technology, Wiley-Interscience, New York (1972), pp. 34-36, indicates that emollients comprise a long list of materials which may be classified in the following types:

(1) Hydrocarbon oils and waxes;
(2) Silicone oils;
(3) Triglyceride esters;
(4) Acetoglyceride esters;
(5) Ethoxylated glyceride;
(6) Alkyl esters;
(7) Alkenyl esters;
(8) Fatty acids;
(9) Fatty alcohols;
(10) Fatty alcohol ethers;
(11) Ether-esters;
(12) Lanolin and derivatives;
(13) Polyhydric alcohols (polyols) and polyether derivatives;
(14) Polyhydric alcohol (polyol) esters;
(15) Wax esters;
(16) Beeswax derivatives;
(17) Vegetable waxes;
(18) Phospholipids;
(19) Sterols; and
(20) Amides.

Lanolin is the unctuous secretion of the sebaceous glands of sheep which is deposited onto the wool fibers. It softens the fleece and serves to protect the fleece against the elements. It is a wax, not a fat. It is a complex mixture of esters, di-esters and hydroxy esters of high molecular weight lanolin alcohols (69 aliphatic alcohols ($C_{12}$-$C_{36}$) and 6 sterols have been identified in lanolin) and high molecular weight lanolin acids (approximately 138 acids ($C_7$-$C_{41}$) have been identified in lanolin). Lanolin is a by-product of the wool-scouring industry.

Wool grease constitutes 10-15% of the weight of sheared wool, depending on the breed of sheep, anatomical area sheared, inner and outer fleece, and season. The average composition of Australian fleeces is 11-16% grease, 6-8% suint (potassium salts of various organic and inorganic acids in the sweat), 10-12% water, 8-19% dirt and 49-61% wool fiber. One hundred pounds of wool yield about 2 to 4 pounds of lanolin. Lanolin is recovered by wool-scouring, followed by separation and purification which may include acid cracking or centrifugal washing, neutralization, removal of soaps, filtration, bleaching and deodorization.

Lanolin is an effective emollient, which by subjective evaluation, effects softening and improvement of dry or rough skin caused by lack of sufficient natural moisture retention. Idson, B. ("What is a moisturizer?", Amer. Perf. Cosm. 87: 33-35 (Aug. 1972)) reported that lanolin causes the water in the skin to build up to its normal level of 10-30% by retarding, without completely inhibiting, trans-epidermal moisture loss.

A relative quantitative evaluation of the occlusive effect of lanolin and other cosmetic materials on the transpiration of moisture from human skin was made by Powers et al. ("A study of the effect of cosmetic ingredients, creams and lotions on the rate of moisture loss from the skin", Proc. Sci. Sect. TGA, No. 28, 21-26 (Dec. 1957)). In particular, lanolin was applied to the inner surface of the forearm (5.0-6.25 mg/cm$^2$, equivalent to a film thickness of 54-68 microns), and was covered with a 28 mm diameter glass desiccator containing silica gel. The uptake of water was determined by weighing the miniature desiccator after specific time intervals. All results were obtained under conditions of zero relative humidity. Lanolin caused a 32% reduction in moisture loss from the skin and lanolin oil a 22% reduction, indicating a mild occlusive effect for these materials as opposed to the extreme barrier effect of petrolatum (48% reduction in moisture loss).

Unfortunately, lanolin, per se, is not satisfactory as a skin treatment product because of its high viscosity, tackiness, and high drag property, thereby making it aesthetically unacceptable to consumers and too difficult to spread onto the skin to be widely accepted.

Thus, historically, lanolin has been used as an auxiliary emulsifier in water-in-oil systems such as the traditional cold creams. In addition to performing as an auxiliary emulsifier, it improves the feel of oil and petrolatum base systems of this type and imparts elegance and a silky smooth texture to the film on the skin. It also modifies the moisture permeability of the extremely occlusive hydrocarbons used in these systems and permits some diffusion of water vapor through the film. This property is related to the fact that lanolin contains a high concentration of hydroxy fatty acid esters of which about 80% are branched. In this respect it resembles human sebum and can in fact duplicate many of the functions of that substance when applied to the skin in cosmetic formulations.

In humans, the branched chain fractions of sebum are at their greatest in the skin of the fetus and diminish with age, becoming much reduced in adults principally because these fatty acids are not derived from metabolism but are by-products of the actual keratinization process, a process which decreases with age. Lanolin can therefore be thought of as supplementing these reduced branched chain fatty acids and as a beneficial emollient, softening and super-fatting agent. Lanolin finds significant uses in lipstick and eye make-up preparations where its co-solvent and film modifying properties are exploited, almost certainly due to its complex branched ester composition. Typically, it reduces sweating or separation of components in pigmented systems. As might be expected, it is also very effective as a wetting and dispersing agent for pigmented medicaments (zinc oxide, calamine, etc.), and hydrocarbon-based ointments can be easily formulated if relatively large quantities of lanolin are included.

The derivatives of lanolin have also been extensively used as emollients. The derivatives of lanolin can be divided into two classes: physical derivatives, which are the result of physical separation processes such as fractional solvent crystallization and chemical derivatives, which are the result of chemical modification of lanolin, per se, and hydrolysis of lanolin to fatty acids and fatty alcohols.

Probably, the best-known of the physical derivatives is lanolin oil, i.e. the liquid esters of lanolin, which is produced by the fractional solvent crystallization of lanolin. Lanolin oil has reduced stickiness and drag, as compared to lanolin, but it too is not satisfactory, per se, as a skin treatment product due to its great fluidity and poor adhesion to the skin. Nonetheless, lanolin oil has good solubility in mineral oil and esters, and good solubility in hydrocarbon aerosol propellants, which, as might be expected, lead to its principal uses in baby oils, brillantines, etc. where clarity is desirable. It is often blended with isopropyl myristate for use in bath oils, where its spreading properties are exploited. Its improved gloss and application properties have also resulted in its extensive use in lipsticks and lip glosses.

Illustrative of compositions of lanolin and its derivatives are:

U.S. Pat. No. 2,498,727, to Verblen, which discloses a cosmetic composition comprising an isopropyl palmitate solution of lanolin which may contain up to 50% lanolin. The solution further includes 10 to 15% refined mineral oil and may include up to about 2% of a wax such as spermaceti wax of cetyl alcohol.

U.S. Pat. No. 2,954,325, to von Baumann, which discloses cosmetic preparations containing from about 1 to about 50% by weight of rendered, purified mink oil having properties which make them superior to prior cosmetic preparation. Thus, it is contended that ointments, salves and creams prepared from a base containing this material have skin softening and penetrating characteristics substantially greater than those imparted by other animal or vegetable oils and fats, as, for instance, lanolin. Nonetheless, a lipstick base which includes, among other ingredients, mink oil and lanolin is disclosed.

U.S. Pat. No. 3,210,248, to Feldman, which discloses an emollient composition in the form of a homogeneous ointment consisting essentially of lanolin alcohols, microcrystalline white wax and a liquid fatty acid ester (e.g., isopropyl myristate or isopropyl palmitate). Preferably, the composition consists essentially of a homogeneous gel of from about 20 to about 40% by weight of lanolin alcohols, from about 10 to about 25% by weight of a microcrystalline white wax and from about 35–55% by weight of the liquid fatty acid ester.

U.S. Pat. No. 3,609,102, to Schlossman, which discloses a freeze-thaw stable transparent gel composition, useful as an emollient base for cosmetics, perfume and pharmaceuticals. The transparent gel has an optical multicolored effect and consists essentially of a clear, continuous, aqueous or aqueous/lower aliphatic water-miscible alcoholic first polar solvent phase and a second nonpolar oil phase. The second oil phase being comprised of a plurality of differently colored discrete macroscopic globular, oil-soluble, first polar phase insoluble emollient bodies dispersed throughout said first phase. The first phase comprising a polar solvent and a polymer dissolved therein, the polymer imparting high viscosity to the composition with a Bingham yield value sufficient to retain the second phase in semisolid to solid mass dispersion, which is not pourable. The polymer is methyl cellulose, hydroxyethyl cellulose, hydroxypropyl cellulose, a neutralized salt of an acidic copolymer of acrylic acid and polyallyl sucrose, or a neutralized salt of an acidic copolymer of ethylene and maleic anhydride. The oil phase material is petroleum jelly, cocoa butter, water-insoluble lanolin derivatives or mixtures thereof.

U.S. Pat. No. 3,666,857, to Russell, which discloses aqueous compositions containing lanolin oil, wherein the lanolin oil is employed as an emollient and conditioner component of the composition, as in the case of shampoos and other detergent products. The lanolin oil is solubilized in water with a combination of (A) fatty acid soaps and/or synthetic detergents, (B) a polyoxyethylene ether of lanolin alcohol condensed with 16 moles of ethylene oxide and (C) a higher fatty acid alkanolamide.

U.S. Pat. No. 4,386,067, to Guillon, which discloses that while it has long been known that vegetable and animal oils can be used for beauty-care purposes, it is more advantageous to incorporate non-saponifiable fractions of vegetable or animal oils either instead of or along with the oils themselves. Beauty-care compositions which may incorporate these non-saponifiable fractions include hand creams and lipsticks, which may include lanolin.

U.S. Pat. No. 4,672,074, to Harendza-Harinxma, which discloses a salve formulation for the topical treatment of inflammations and lesions of the human skin due to Herpes type virus which includes Indomethacin in a concentration of 0.1% to 3% by weight as the active ingredient which is suspended in a carrier comprising: zinc oxide in a concentration of 40% by weight; petrolatum in a concentration of 14% by weight; lanolin in a concentration of 10% by weight; talc in a concentration of 12% by weight; and cod liver oil in a concentration of 21% by weight.

British Patent No. 572,318, to Croda Limited, discloses an emulsion base comprising: a hydrogenated glyceride; wool wax alcohol or alcohols; and natural or synthetic esters of wool wax alcohol or alcohols. Wool wax alcohol or alcohols include Hartolan ®, crude cholesterol (Dastar ® or Kathro ®), agnosterol, lanosterol and lano-octadecyl or lanyl alcohols. Natural esters of wool wax alcohol or alcohols are represented by anhydrous lanolin; suitable synthetic esters are oleates and stearates. Suitable hydrogenated glycerides include hydrogenated oils such as caster, arachis, oil, palm kernel, cotton seed, soya-bean, coconut and sesame oils.

British Published Patent Application No. 2,169,509A, to Tomlin, which discloses a skin treatment cream containing 3 to 5% by weight of beeswax, 3 to 5% by weight of whales' wax, 15 to 25% by weight of lanolin, 30 to 40% by weight of almond oil and 30 to 40% by weight of rose water.

Japanese Published Patent Application No. 53-147803, to Daiichi Kogyo Seiyaku, which discloses a softening and anti-curling agent for paper which contains as the essential ingredients at least one material selected from (a) lanolin and its alkylene oxide addition products, (b) lanolin alcohol and its alkylene oxide addition products, (c) lanolin fatty acid and its polyhydric alcohol esters, alkanolamides, polyoxyalkyleneglycolesters and soaps, and (d) alkylene oxide addition products of lanolin fatty acid polyhydric alcohol esters. The softening agent is used for the treatment of tissue paper, paper towels, paper diapers, etc. A typical composition comprises 85 parts by weight of water, 3 parts by weight of lanolin, 7 parts by weight lanolin fatty acid monoesters of polyglycerol and 5 parts by weight of lanolin fatty acid triethanolamine soap.

U.S. Pat. No. 539,386, to Hartshorne et al., discloses process for treating (and refining) wool fat which comprise:

(A) mixing wool fat with acetone and separating the constituent which is soluble in cold acetone (product 5) from the constituent which is not soluble in cold acetone (product 4), then contacting product 5 with alcohol and separating the constituent which is soluble in cold alcohol (product 1) from the constituent which is not soluble in cold alcohol (product 3); or (B) mixing wool fat with alcohol and separating the constituent which is soluble in cold alcohol (product 1) from the constituent which is not soluble in cold alcohol (product 2), then contacting product 2 with acetone and separating the constituent which is soluble in cold acetone (product 3) from the constituent which is not soluble in cold acetone (product 4).

Australian Patent No. 135,020, to Sly, discloses high vacuum (pressure below about 0.1 mm Hg), short or unobstructed path (condensing and evaporating surfaces are separated by a substantially free, unrestricted or unobstructed path for the travel of vapors from one surface to the other) distillation of wool grease to produce new compositions of which the two principal fractions are (1) sterols or other compounds possessing a free hydroxyl group and having molecular weights between about 300 and 500, eliminated from the wool grease distilland in the first 15% to distill therefrom; and (2) ester compounds having molecular weights between about 500 and 1000, eliminated from the wool grease distilland after the first 15% and up to about 90% has distilled therefrom.

U.S. Pat. No. 2,725,334, to Conrad et al., discloses a modified lanolin that is practically odorless and completely soluble in mineral oil in concentrations up to 10% at a temperature of 25° C., which is prepared by reacting 40 to 100% of the hydroxyl groups of lanolin with one of the group consisting of acetic anhydride, propionic anhydride, ricinoleic acid and benzoic anhydride, washing out excess acylating media with a wash media, and removing the residual wash media, residual acid and side reaction materials by vacuum distillation.

SUMMARY OF THE INVENTION

It is an object of the present invention to provide a water-free, skin treatment composition in which the emollient concentration is 100 percent so as to provide maximum effectiveness.

It is a further object of the invention to provide a hypoallergenic skin treatment composition.

It is a still further object of the invention to provide a lanolin-based skin treatment composition which is aesthetically acceptable to the consumer.

These and other objects of the invention, as will become apparent hereinafter, have been achieved by the present invention which provides a skin treatment composition comprising from about 10 to about 90% by weight of lanolin and from about 90 to about 10% by weight of lanolin oil.

In a particularly preferred embodiment of the invention there is provided an anhydrous, hypoallergenic skin treatment composition consisting of about 75% by weight of lanolin and about 25% by weight of lanolin oil.

DETAILED DESCRIPTION OF THE INVENTION

The present invention is an uncommon way to formulate a treatment product, especially of lanolin, as it is a distinct departure from the prior art in which conventional emulsified (water-based) systems are used by the cosmetic and pharmaceutical industry. Specifically, the present invention is based on the creation of a water-free, non-emulsified composition which may contain 100% emollient materials for maximum effectiveness.

Lanolin, as previously noted, is a naturally derived product comprised of a mixture of esters, di-esters and hydroxy esters of high molecular weight lanolin alcohols (Table 1) and lanolin acids (Table 2). It is self emulsifying, forming stable water-in-oil emulsions, and absorbs up to two or more times its weight of water.

TABLE 1

| Lanolin Alcohols | |
|---|---|
| Type of Alcohol | No. Indentified |
| A. Aliphatic Alcohols | |
| (1) Normal $CH_3(CH_2)_n OH$<br>(n = 13-33) | 16 |
| (2) Iso $CH_3-CH(CH_3)(CH_2)_n OH$<br>(n = 11-33) | 11 |
| (3) Anteiso $CH_3-CH_2-CH(CH_3)(CH_2)_n OH$<br>(n = 13-31) | 11 |
| (4) Normal 1,2-diols<br>$CH_3-(CH_2)_n CH(OH)-CH_2 OH$<br>(n = 91-22) | 14 |

TABLE 1-continued

Lanolin Alcohols

| Type of Alcohol | No. Indentified |
|---|---|
| (5) Iso 1,2-diols<br>$CH_3-CH-(CH_2)_n-CH-CH_2$<br>$\quad\quad\;\; \mid \quad\quad\quad\quad\;\; \mid \;\;\; \mid$<br>$\quad\quad\; CH_3 \quad\quad\quad\;\; OH\;\; OH$<br>(n = 9-25) | 9 |
| (6) Anteiso 1,2-diols<br>$CH_3-CH_2-CH-(CH_2)_n-CH-CH_2$<br>$\quad\quad\quad\quad\quad\;\; \mid \quad\quad\quad\quad\;\; \mid \;\;\; \mid$<br>$\quad\quad\quad\quad\; CH_3 \quad\quad\quad\;\; OH\;\; OH$<br>(n = 9-23) | 8 |
| B. Sterols | |
| (1) Chloesterol | 1 |
| (2) Dihydrocholesterol | 1 |
| C. Trimethyl Sterols | |
| (1) Lanosterol | 1 |
| (2) Dihydrolanosterol | 1 |
| (3) Agnosterol | 1 |
| (4) Dihydroagnosterol | 1 |

TABLE 2

Lanolin Acids

| Type of Acid | No. Identified |
|---|---|
| (1) Normal<br>$CH_3\!\!-\!\!(CH_2)_{\overline{n}}COOH$<br>(n = 6-36) | 27 |
| (2) Iso<br>$CH_3-CH-(CH_2)_n-COOH$<br>$\quad\quad\;\;\; \mid$<br>$\quad\quad\; CH_3$<br>(n = 4-36) | 17 |
| (3) Anteiso<br>$CH_3-CH_2-CH-(CH_2)_n-COOH$<br>$\quad\quad\quad\quad\quad\;\; \mid$<br>$\quad\quad\quad\quad\; CH_3$<br>(n = 2-36) | 18 |
| (4) Alpha hydroxy normal<br>$CH_3-(CH_2)_n-CH-COOH$<br>$\quad\quad\quad\quad\quad\quad\;\;\; \mid$<br>$\quad\quad\quad\quad\quad\quad\; OH$<br>(n = 7-29) | 23 |
| (5) Alpha hydroxy iso<br>$CH_3-CH-(CH_2)_n-CH-COOH$<br>$\quad\quad\;\;\; \mid \quad\quad\quad\quad\;\; \mid$<br>$\quad\quad\; CH_3 \quad\quad\quad\;\; OH$<br>(n = 7-29) | 12 |
| (6) Alpha hydroxy anteiso<br>$CH_3-CH_2-CH-(CH_2)_n-CH-COOH$<br>$\quad\quad\quad\quad\quad\;\; \mid \quad\quad\quad\quad\;\; \mid$<br>$\quad\quad\quad\quad\; CH_3 \quad\quad\quad\;\; OH$<br>(n = 5-27) | 12 |
| (7) Omega hydroxy normal<br>$HO-CH_2-(CH_2)_n-COOH$<br>(n = 20-34) | 14 |
| (8) Omega hydroxy iso<br>$HO-CH-CH_2-(CH_2)_n-COOH$<br>$\quad\quad\;\;\; \mid$<br>$\quad\quad\; CH_3$<br>(n = 18-32) | 8 |
| (9) Omega hydroxy anteiso<br>$HO-CH_2-CH-(CH_2)_n-COOH$<br>$\quad\quad\quad\quad\;\; \mid$<br>$\quad\quad\quad\;\; CH_3$<br>(n = 19-31) | 7 |

There are many grades of lanolin available, especially anhydrous lanolins. Most companies use a USP grade of anhydrous lanolin when formulating their products. At this level of refinement, adventitious materials may remain in the lanolin and it will still meet the USP grade requirements. While this poses no threat to the general population, the dermatologically sensitive population may experience an allergic reaction to a cruder grade of lanolin. In this regard, free lanolin alcohols have been identified as the allergen (Takano et al., Allergens of Lanolin: parts I and II, J. Soc. Cosmet. Chem., 34, 99-125 (March/April 1983)), especially the diols. Moreover, in combination with detergent residues (residues from the wool scouring process, etc.), the incidence of an allergic reaction increases. For example, Clark et al., Lanolin With Reduced Sensitizing Potential, Contact Dermatitis 1977: 3: 69-74, has shown that as little as 0.1% of detergent may increase significantly the detectable incidence of hypersensitivity, in subjects with a history of lanolin allergy, in the presence of moderate amounts of free alcohols (e.g. about 9%). Higher concentrations of detergents do not result in any further increase. When the free fatty alcohol content is low (e.g., about 2.2%), the addition of detergent has only a slight effect; and when the free fatty alcohol content is high (as in wool alcohols), the addition of detergent has little, if any, observable effect.

Nonetheless, since the incidence of primary specific lanolin allergy amongst the general population has been quantified at 5.5±4.2 per million (Clark, E.W., Estimation of the general incidence of specific lanolin allergy, Journal of the Society of Cosmetic Chemists, 26, pp. 323-335 (1975)), and since lanolin, per se, has a lower content of free alcohols than many of the chemical derivatives thereof, the use of lanolin, especially pure anhydrous lanolin, would provide a composition meeting reasonable criteria for hypoallergenicity. Suitable anhydrous lanolins include Clearlan 1650 ® and Sparklelan 1656 ® (both products of Quantum Chemical Corporation, a division of Emery). Product specifications for these materials are set forth in Table 3.

TABLE 3

| Specification | Clearlan 1650 | Sparklelan 1656 |
|---|---|---|
| Color (Gardner), Max. | 9 | 12 |
| Free Fatty Acid (USP as oleic), % Max. | 0.56 | 0.56 |
| Moisture (USP), % Max. | 0.25 | 0.25 |
| Melting Range (USP Class II), °C. | 38-44 | 38-44 |
| Ash (USP), % Max. | 0.1 | 0.1 |
| Iodine Value (USP, 0.78-0.82 g. sample) | 18-36 | 18-36 |

Lanolin oil, as previously noted, is produced by the removal of the solid esters from lanolin using low temperature fractional solvent crystallization, i.e. lanolin oil is a mixture of liquid lanolin esters (a liquid wax). There are significant physical and chemical differences between lanolin and lanolin oil, in that the latter contains a higher concentration of lower molecular weight, branched-chain, hydroxy compounds. The viscosity of lanolin oil may range from 1400 to 4000 centipoises at 25° C, depending on the different crystallizing solvents used (typically lower molecular weight ketones and esters such as acetone, methyl ethyl ketone and ethyl acetate) and the particular lanolin used by different companies. Lanolin oil is readily available commercially under such trade names as Argonol ® 45, 50 and 60 (Westbrook), Fluilan ® (Croda USA), Lanex ®

(Croda USA), Lanogene ® (Amerchol), Lanoil (Lanaetex), Lanolin Oil (Brooks Industries), Lanolin Oil (Laserson & Sabetay), Lantrol ® 1673 or 1674 (Emery), Lipolan R ® (Lipo), Protalan Oil ® (Protameen), Reolan ® (Takasago), Ritalan ® (RITA), Stellanol ® (Stella) or Vigilan ® (Fanning). The hypoallergenic, oil soluble, liquid fraction of anhydrous lanolin, USP cosmetic grade sold under the trade name Lantrol ® 1674 has been found to be particularly desirable for preparation of the present compositions. Product specifications for this material are set forth in Table 4.

TABLE 4

| Specification | Value |
| --- | --- |
| Free Fatty Acid (USP as oleic) % Max. | 0.56 |
| Color (Gardner), Max. | 10 |
| Odor | nearly odorless |
| Moisture (USP), % Max. | 0.25 |
| Ash (USP), % Max. | 0.10 |
| Iodine Value (USP, 0.78–0.82 g. sample) | 18–36 |
| Cloud Point, °F. Max. (ASTM D97-47) | 68 |

The compositions of the present invention may be formed by blending about 10 to about 90% by weight of lanolin with about 90 to about 10% by weight of lanolin oil, preferably about 50 to about 90% by weight of lanolin is blended with about 50 to about 10% by weight of lanolin oil, most preferably, about 75% by weight of lanolin is blended with about 25% by weight of lanolin oil.

While it is possible to blend other ingredients, e.g., fragrances, colorants, etc., into the presently contemplated compositions, it is much preferred that the compositions consist solely of lanolin and lanolin oil. This avoids the introduction of possible allergens or irritants into the compositions, avoids the possibility of adverse ingredient interactions, and avoids the possibility of additional solubilizing agents being required so as to allow certain ingredients to be added.

Preferably, the present compositions are anhydrous, i.e. have a maximum water content of 0.25% by weight. This is most easily achieved by blending initially anhydrous ingredients under carefully controlled environmental conditions. The substantial exclusion of water from the present compositions provides numerous benefits not the least of which are the avoidance of bacterial growth due to a lack of water, thus enhancing shelf life; and the avoidance of substantial hydrolysis of the esters, thus avoiding generation of the primary allergens associated with lanolin, i.e. the lanolin alcohols.

The present compositions may be readily prepared by heating the lanolin, e.g., Clearlan ® 1650 or Sparklelan ® 1656, to a temperature above its melting point (38–44° C.), e.g., 50° C., and then adding the lanolin oil, which may have been pre-heated to the same temperature as the lanolin, with mild agitation until a homogeneous liquid is formed. The homogeneous mass may then be cooled to room temperature (about 20° C.) to form a semi-soft solid having about the same consistency as petrolatum. Preferably, the mixture is first packaged in the desired containers and then allowed to cool.

The present compositions are characterized by ease of spreadability on the skin to form a partially occlusive film. This partially occlusive coating permits rehydration of dry skin by inhibiting transepidermal moisture loss. However, by permitting some passage of water therethrough, it prevents an overhydration of the skin which can cause edema. Additionally, oxygen may pass through the coating thus preventing the propagation of anaerobic bacteria, a factor which may be of importance where the skin is cracked and broken due to excessive dryness and/or scratching by the patient. While the present compositions find their primary utility in the treatment of "dry" skin, they have also been found useful in the treatment of numerous skin lesions such as bed sores and diabetic ulcers.

The present compositions may be applied at a rate of about 1 gram per 15–25 $cm^2$, and spread by simple rubbing. Of course, greater or lesser amounts may be utilized, although increased amounts do not necessarily produce increased benefits. The present compositions may be applied twice a day, but greater or lesser numbers of applications may be utilized depending on the needs of the patient, as may be influenced by the activities in which the patient engages and/or the bathing frequency of the patient.

What is claimed is:

1. An anhydrous skin treatment composition consisting essentially of:

(A) from about 10 to about 90% by weight of lanolin; and (B) from about 90 to about 10% by weight of lanolin oil.

2. The anhydrous skin treatment composition according to claim 1, wherein said lanolin is present in an amount of from about 50 to about 90% by weight and said lanolin oil is present in an amount of from about 50 to about 10% by weight.

3. The anhydrous skin treatment composition according to claim 2, wherein said lanolin is present in an amount of about 75% by weight and said lanolin oil is present in an amount of about 25% by weight.

4. The anhydrous skin treatment composition according to claim 1, wherein the total of components (A) and (B) is 100% by weight.

5. The anhydrous skin treatment composition according to claim 2, wherein the total of components (A) and (B) is 100% by weight.

6. The anhydrous skin treatment composition according to claim 3, wherein the total of components (A) and (B) is 100% by weight.

7. The anhydrous skin treatment composition according to claim 1, wherein said composition is hypoallergenic.

8. The anhydrous skin treatment composition according to claim 2, wherein said composition is hypoallergenic.

9. The anhydrous skin treatment composition according to claim 3, wherein said composition is hypoallergenic.

10. An anhydrous, hypoallergenic skin treatment composition consisting of:

(A) from about 10 to about 90% by weight of lanolin; and (b) from about 90 to 10% by weight of lanolin oil.

11. The anhydrous, hypoallergenic skin treatment composition according to claim 10, wherein said lanolin is present in an amount of from about 50 to about 90% by weight and said lanolin oil is present in an amount of from about 50 to about 10% by weight.

12. The anhydrous, hypoallergenic skin treatment composition according to claim 11, wherein said lanolin is present in an amount of about 75% by weight and said lanolin oil is present in an amount of about 25% by weight.

* * * * *